United States Patent [19]
Yang

[11] Patent Number: 6,126,942
[45] Date of Patent: Oct. 3, 2000

[54] HERBAL COMPOSITIONS FOR HEPATIC DISORDERS

[75] Inventor: Yi Fan Yang, Surry Hills, Australia

[73] Assignee: Cathay Herbal Laboratories, Pty., N.S.W., Australia

[21] Appl. No.: 08/983,616

[22] PCT Filed: Jul. 10, 1996

[86] PCT No.: PCT/AU96/00434

§ 371 Date: Aug. 17, 1998

§ 102(e) Date: Aug. 17, 1998

[87] PCT Pub. No.: WO97/02831

PCT Pub. Date: Jan. 30, 1997

[30] Foreign Application Priority Data

Jul. 10, 1995 [AU] Australia ................. PN 4111

[51] Int. Cl.[7] ................. A61K 35/78; A61K 9/20
[52] U.S. Cl. ................. 424/195.1; 424/464; 514/893; 514/894
[58] Field of Search ................. 424/195.1, 464; 514/893, 894

[56] References Cited

U.S. PATENT DOCUMENTS 4,886,666 12/1989 Liu ................. 424/195.1

FOREIGN PATENT DOCUMENTS 2103016 5/1987 Japan .
1102092 4/1989 Japan .

OTHER PUBLICATIONS

Chung Kuo Chung Hsi I Chieh Ho Tsa Chi (China) Sep. 1993 13(9) Xiong L L "Therapeutic effects of combined therapy of Salvia Miltiorrhizae and Polyporus umbellatus polysaccharide in the treatment of chronic hepatitis B." p. 533–555, 516–517 Abstract.
Chung Hsi I Chieh Ho Tsa Chih (China) Apr. 1991 11(4) p225–6 (Abstract) Zhang, Y.H. et al "Effect of Polyporus umbellatus polysaccharide on function of macrophages in the peritoneal cavities of mice liver with lesions".
Chung Hsi I Chieh Ho Tsa Chi (China) Feb. 1991 11(2) p102–4 (Abstract) Qi, X.G., "Protective mechanism of Salvia miltiorrhiza and Paeonia lactiflora for experimental liver damage".
Chung Kuo Chung Yao Tsa Chih (China) Dec. 1992 17(12) p. 749–751 (Abstract) Yu, Z.P. et al. "Effects of Salvia miltiorrhiza Bunge on isolated perfused liver and protal vein of rats".
Journal of Ethnopharmacology 1987 19 p103–110, Ling–Ling Yang et al. "Antihepatoxic Actions of Formosan Plant Drugs".
Cancer Letters, 1986, 30, p. 143–151. Hajime Ohigashi et al. "Search for Possible Antitumour Promotors by Inhibition of the 12–0–Tetradecanoylphorbol–13–Acetate–Induced Epstein–Barr Virus Activation; Ursolic Acid and Oleanolic Acid from an Anti–inflammatory Chinese Medicinal Plant, *Glechoma Hederaceae L.*".
Planta Medica, 1994, vol. 60, p. 414–416 Yoshikazu Kondo et al. "Suppression of Chemically and Immunologically Induced Hepatic Injuries by Gentiopicroside In Mice".
Planta Medica, 1988, vol. 54, p. 413–414, Shean Farn Yeh et al. "Effects of Anthraquinones of *Polygonum cuspidatum* on HL–60 Cells".
A Textbook of Natural Medicine, 1993, vol. I, Joseph E. Pizzorno and Michael T. Murray, "Glycyrrhiza" V glycyr 3, Bastyr College Publications; Seattle, Washington.
Medicinal Plants in China, 1989, World Health Organization (WHO) Regional Publications Western Pacific Series No. 2, MANILA, pp. 30, 42, 48, 71, 84, 96, 97, 139, 150.
Healing with Chinese Herbs, 1990, Richard Hyatt, Healing Arts Press; Rochester, Vermont, pp. 113, 122, 133, 134, 139, 142.
Chung Hsi I Chieh Ho Tsa Chih (China), Aug. 1987, vol. 7(8), p. 483–4, Wang, S.L., et al, "Effects of Crataegus pinnatifidae, Astragalus membranaceus and Acanthopanax senticosus on cholesterol metabolism in the guinea pig". (Abstract).
Indian Journal of Exp Biol, Jul. 1989, vol. 27(7), p. 631–4, Dua et al., "Adaptogeaic activity of Indian Panax pseudo-ginseng".

*Primary Examiner*—Leon B. Lankford, Jr.
*Assistant Examiner*—Christopher R. Tate
*Attorney, Agent, or Firm*—Fenwick & West LLP

[57] ABSTRACT

The present invention relates to compositions comprising the herbs *Salvia miltiorrhiza* and *Polyporus umbellatus,* or extracts thereof, which are useful in treating hepatic disorders, particularly those with viral aetiology. The compositions may comprise other herbs or their extracts, and may be useful for treating hepatic disorders other than those caused by viral infection.

13 Claims, No Drawings

HERBAL COMPOSITIONS FOR HEPATIC DISORDERS

TECHNICAL FIELD

This invention relates to a new medicinal compositions and methods of treating hepatic disorders.

BACKGROUND ART

Hepatic disorders, in particular those caused by viral infections, are a major health problem and the successful treatment of hepatic diseases poses a great challenge to the medical profession. With respect to hepatic diseases caused by viral infection, currently patients in advanced stages of the infection cycle (chronic hepatitis) with, for example, hepatitis C virus are treated with Interferon ("IFN") with only about 25% success rate. IFN is not readily available to patients and a six-month course of IFN therapy costs about $3000. It also gives rise to several side-effects such as severe flu symptoms, lethargy, hair loss and undesirable tastes in the mouth. IFN acts against the virus via the immune system and does not reverse any physiological abnormalities or damage caused by the infection eg. hepatic cirrhosis, diminished spleen function, etc. Furthermore, as there is a number of hepatic disorders which are not caused by viral infection, the administration of INF to patients with non-viral hepatic disorders would be ineffective.

It is an object of the present invention to provide an effective method of and medication for, treatment of both viral and non-viral hepatic disorders which avoids or at least ameliorates one or more of the disadvantages of current treatments.

SUMMARY OF THE INVENTION

According to a first aspect, the invention cat in a composition comprising the herbs *Salvia miltiorrhiza* and *Polyporus umbellatus,* or extracts thereof.

In a preferred embodiment the invention consists in a composition which further comprises at least one of the herbs *Curcuma longa, Astragalus membranaceus, Loranthus parasiticus* and *Polygonum cuspidatum,* or extracts thereof In another preferred embodiment the invention consists in a composition which further comprises at least one of the herbs *Poria cocos, Artemisia capillaris, Taraxacum mongolicum, Paeonia lactiflora, Panax pseudoginseng, Bupleurum falcatum, Cratagus pinnatifida, Glechoma longituba, Codonopsis pilosula, Lycium barbarum, Zizyphus jujuba, Gentiana manshurica* and *Glycyrrhiza uralensis,* or extracts thereof.

According to a second aspect the invention consists in a composition comprising the herbs *Salvia miltiorrhiza, Polyporus umbellatus, Poria cocos, Artemisia capillaris Taraxacum mongolicum, Paeonia lactiflora, Panax pseudoginseng, Bupleurum falcatum, Crataegus pinnatifida, Curcuma longa, Glechoma longituba, Astragalus membranaceus, Codonopsis pilosula, Loranthus parasiticus, Lycium barbarum, Polygonum cuspidatum, Zizyphus jujuba, Gentiana manshurica* and *Glycyrrhiza uralensis,* or extracts thereof.

According to a third aspect, the invention consists in a method of treating hepatic disorders comprising the step of administering to a patient requiring such treatment any one of the compositions described above.

Preferably, the hepatic disorder treated is a non-viral hepatic disorder such as alcoholic hepatitis, cirrhosis or autoimmune liver disease.

More preferably the hepatic disorder treated is caused by a viral infection such as hepatitis virus A, B or C infection.

The treatment can be therapeutic or prophylactic, and may be administered orally or parenterally. The parenteral route could be topical, intravenous or subcutaneous. The treatment may be delivered in a single bolus dose, multiple doses or via a slow release device or a depot.

DESCRIPTION OF THE PREFERRED EMBODIMENT

In a preferred embodiment of the invention, the composition of the invention comprises *Salvia miltiorrhiza* and *Polyporus umbellatus* in the proportion of from 1:1 to 1:5 or 5:1. For example, these herbs may each comprise from 6 to 30% of the total weight of the herbal composition, the balance being made up for example by other herbs, preferably *Curcuma longa* (2–10%), *Astragalus membranaceus* (5–30%), *Loranthus parasiticus* (5–30%) and *Polygonum cuspidatum* (3–20%).

Although the administration of a composition containing only Salvia and Polyporus will be effective in treating chronic hepatitis, the synergism between all the herbs render the administration of a combination containing each herb desirable.

Thus, in a more preferred embodiment, the composition comprises each herb combined in the proportions given in Table 1.

Various parts of each herb may be used and these include the root, stem, fruit or whole plant or tuber.

The availability of the herbs and ease of concentrating the extracts provides a cheaper, alternative medicine which also does not give rise to undesirable side-effects. There is also a higher incidence of cure in that liver cirrhosis may be reversed and hepatic enzyme levels and microcirculation may be normalised, thus rendering this form of treatment applicable not only to hepatic disorders caused by virus infection but also those disorders caused by other agents and causes which can compromise liver function and microcirculation.

The invention will now be described with reference to the following example to illustrate a preferred embodiment only and does not serve to limit the invention.

EXAMPLE 1

One method of preparing the compositions of the invention is to mix the cut, ground or powdered herbs listed in Table 1 and boil the mixture in a vat. The liquid is thus concentrated into a paste which can subsequently be processed further into tablets averaging about 170 mg each, using procedures which conform to standard, General Manufactured Products (GMP) guidelines.

TABLE 1

Medicinal composition comprising herbal extracts in pill-form.

| Powdered Herbs | Weight |
| --- | --- |
| *Polyporus umbellatus* root | 16 mg |
| *Salvia miltiorrhiza* root | 14 mg |
| *Artemisia capillaris* Thunb. | 14 mg |
| *Poria cocos* root | 12 mg |
| *Taraxacum mongolicum* plant | 12 mg |
| *Paeonia lactiflora* root | 10 mg |
| *Astragalus membranaceus* root | 10 mg |
| *Loranthus parasiticus* stem | 10 mg |

TABLE 1-continued

Medicinal composition comprising herbal extracts in pill-form.

| Powdered Herbs | Weight |
|---|---|
| *Glechoma longituba* plant | 9 mg |
| *Codonopsis pilosula* plant | 9 mg |
| *Polygonum cuspidatum* root | 9 mg |
| *Gentiana manshurica* plant | 9 mg |
| *Bupleurum falcatum* root | 7 mg |
| *Crataegus pinnatifida* fruit | 7 mg |
| *Lycium barbarum* fruit | 7 mg |
| *Zizyphus jujuba* fruit | 7 mg |
| *Curcuma longa* tuber | 5 mg |
| *Panax pseudoginseng* root | 3 mg |
| *Glycyrrhiza uralensis* root (colouring/coating) | 5 mg |

Consumption of 8 tablets three times daily, 30–60 minutes prior to meals with warm water is recommended for adults. Children may be prescribed half the adult dosage. The dosage and the formulation may be varied according to the condition treated and the concentration of active ingredients used in each dose. Thus, the dosage may range from 3 to 10 tablets three times daily, or more or less frequently as required. The compositions may also be administered as a liquid or in the form of a slow release formulation

EXAMPLE 2

An alternative method of preparing the compositions of the invention is to powder the herbs listed in Table 1 by crushing and grinding each herb after drying it in a machine in a known, conventional manner. The individual components are then formulated into tablets.

EXAMPLE 3

A tablet form of the composition prepared according to Example 1 was evaluated in patients with chronic hepatitis C (CHCV) using a double-blind, randomised placebo controlled protocol. Treatment involved 5 tablets tds for 6 months with monthly assessment by a hepatologist and traditional Chinese medicine specialist. 58 patients were assessed, 43 randomised to treatment and 40 completed therapy.

| Results | Treated Group | Placebo Group |
|---|---|---|
| (n) Age (yrs) | 10; 40.4 | 20; 40.9 |
| Male % | 59.1 | 59.1 |
| Duration of HCV (mths) | 92 | 83 |
| Alcohol g/d; Past interferon | 20; | 20; |
| Initial/final ALT | 120/82 | 102/102 |

Treatment with the composition of the present invention resulted in a significant (p<0.03) fall in ALT whereas treatment with placebo did not (Wilcoxon matched pairs signed-rank test for non-parametric date). 4 patients in the treatment group normalised their ALT but relapsed on cessation of drug. Treatment had no effect on ALP, Haemoglobin, WCC and platelets. The results of the study demonstrate that the composition was capable of modifying disease activity in CHCV. Further studies of the treatment on HCV-RNA and histological changes are supported by these preliminary results.

A person skilled in the art will understand that the therapeutic effects of the composition result from a plurality of active agents in each herb which when combined, act synergistically to enhance efficacy. It will also be understood that compositions comprising all or a selection of such active agents, preferably in pure form, are also contemplated herein, as are liquid formulations of the composition and formulations which are suitable for slow release administration. Thus it will be understood that the compositions of the invention can be administered orally, intravenously, subcutaneously, topically or by other known means The compositions are effective in treating hepatic disorders generally, irrespective of their aetiology since the compositions act at least in part to improve liver function and microcirculation. The compositions may also exert their effect prophylactically, by preventing or minimising the adverse effects of viral infection or the action of other agents which cause liver dysfunction. Therefore, the treatment of hepatic disorders caused by viral infection, autoimmune reactions, drug intake and the like are contemplated herein.

The invention may be embodied in various other forms which are understood by those skilled in the art.

What is claimed is:

1. A medicinal composition for treating hepatitis comprising effective amounts of the herbs *Salvia miltiorrhiza* root, *Polyporus umbellatus* root, *Poria cocos* root, *Artemisia capillaries* Thunb. plant, *Taraxacum mongolicum* plant, *Paeonia lactiflora* root, *Panax pseudoginseng* root, *Bupleurum falcatum* root, *Crataegus pinnatifida* fruit, *Curcuma longa* tuber, *Glechoma longituba* plant, *Astragalus membranaceus* root, *Codonopsis pilosula* root, *Loranthus parasiticus* stem, *Lycium barbarum* fruit, *Polygonum cuspidatum* root, *Zizyphus jujuba* fruit, *Gentiana manshurica* plant and *Glycyrrhiza uralensis* root.

2. A composition of herbs according to claim 1 including approximately 14 parts *Salvia miltiorrhiza* root, 16 parts *Polyporus umbellatus* root, 12 parts *Poria cocos* root, 14 parts *Artemisia capillaris* Thunb. plant, 12 parts *Taraxacum mongolicum* plant, 10 parts *Paeonia lactiflora* root, 3 parts *Panax pseudoginseng* root, 7 parts *Bupleurum falcatum* root, 7 parts *Crataegus pinnatifida* fruit, 5 parts *Curcuma longa* tuber, 9 parts *Glechoma longituba* plant, 10 parts *Astragalus membranaceus* root, 9 parts *Codonopsis pilosula* root, 10 parts *Loranthus parasiticus* stem, 7 parts *Lycium barbarum* fruit, 9 parts *Polygonum cuspidatum* root, 7 parts *Zizyphus jujuba* fruit, 9 parts *Gentiana manshurica* plant and 5 parts *Glycyrrhiza uralensis* root.

3. A composition according to claim 1, wherein the composition is in the form of a tablet.

4. A composition according to claim 1, wherein the composition is in the form of a liquid.

5. A composition according to claim 1, wherein *Salvia miltiorrhiza* and *Polyporus umbellatus* each comprise from 6 to 30% of the total weight of the composition.

6. A method of treating hepatic disorders comprising the administration to a patient requiring such treatment a composition according to claim 1.

7. A method of treating hepatic disorders caused by a hepatitis C virus infection comprising the administration to a patient requiring such treatment a composition according to claim 1.

8. A method according to claim 7, wherein the hepatic disorders result from chronic hepatitis.

9. A method according to claim 7, where the composition is administered parenterally.

10. A method according to claim 7, wherein the treatment is therapeutic.

11. A method according to claim 7, wherein the treatment is prophylactic.

12. A method of preparing a medicinal composition for treating hepatitis comprising the steps of:
   a. mixing effective amounts of the following cut, ground or powdered herbs: *Salvia miltiorrhiza* root, *Polyporus umbellatus* root, *Poria cocos* root, *Artemisia capillaris* Thunb. plant, *Taraxacum mongolicum* plant, *Paeonia lactiflora* root, *Panax pseudoginseng* root, *Bupleurum falcatum* root, *Crataegus pinnatifia* fruit, *Curcuma longa* tuber, *Glenchoma longituba* plant, *Astragalus membranaceus* root, *Codonopsis pilosula* root, *Loranthus parasiticus* stem, *Lycium barbarum* fruit, *Polygonum cuspidatum* root, *Zizyphus jujuba* fruit, *Gentiana manshurica* plant and *Glycyrrhiza uralensis* root.

13. A method according to claim 12, further comprising the steps of preparing said medicinal composition into a paste and formulating said paste into tablets.

* * * * *